(12) United States Patent
Kee et al.

(10) Patent No.: US 9,950,046 B2
(45) Date of Patent: *Apr. 24, 2018

(54) METHODS OF TREATMENT USING ALPHA-1-ANTITRYPSIN COMPOSITIONS

(71) Applicant: CSL Behring L.L.C., King of Prussia, PA (US)

(72) Inventors: Scott M. Kee, Bourbonnais, IL (US);
Paul I. Cook, Kankakee, IL (US);
James R. Smith, Bourbonnais, IL (US);
Robert Kling, Bourbonnais, IL (US);
Scott A. Fowler, Apex, NC (US);
David Weber, Bradley, IL (US)

(73) Assignee: CSL Behring L.L.C., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/074,266

(22) Filed: Mar. 18, 2016

(65) Prior Publication Data

US 2017/0042986 A1   Feb. 16, 2017

Related U.S. Application Data

(60) Continuation of application No. 14/802,885, filed on Jul. 17, 2015, now Pat. No. 9,320,783, which is a continuation of application No. 14/223,010, filed on Mar. 24, 2014, now abandoned, which is a continuation of application No. 13/385,642, filed on Feb. 28, 2012, now Pat. No. 8,722,624, which is a continuation of application No. 12/855,721, filed on Aug. 13, 2010, now Pat. No. 8,124,736, which is a division of application No. 10/334,303, filed on Dec. 31, 2002, now Pat. No. 7,777,006.

(51) Int. Cl.
| | | |
|---|---|---|
| *A61K 38/57* | (2006.01) | |
| *A61K 9/19* | (2006.01) | |
| *C07K 14/81* | (2006.01) | |
| *B01D 15/36* | (2006.01) | |
| *B01D 15/32* | (2006.01) | |
| *G01N 30/46* | (2006.01) | |

(52) U.S. Cl.
CPC .............. *A61K 38/57* (2013.01); *A61K 9/19* (2013.01); *B01D 15/327* (2013.01); *B01D 15/363* (2013.01); *C07K 14/8125* (2013.01); *G01N 30/461* (2013.01)

(58) Field of Classification Search
None
See application file for complete search history.

(56) References Cited

U.S. PATENT DOCUMENTS

| | | |
|---|---|---|
| 3,293,326 A | 12/1966 | Schultze et al. |
| 3,301,842 A | 1/1967 | Schultze et al. |
| 4,379,087 A | 4/1983 | Coan et al. |
| 4,439,358 A | 3/1984 | Coan et al. |
| 4,440,679 A | 4/1984 | Fernandes et al. |
| 4,623,717 A | 11/1986 | Fernandes et al. |
| 4,629,567 A | 12/1986 | Bollen et al. |
| 4,656,254 A | 4/1987 | Shearer et al. |
| 4,684,723 A | 8/1987 | Dove et al. |
| 4,697,003 A | 9/1987 | Coan |
| 4,749,783 A | 6/1988 | Jordan et al. |
| 4,820,805 A | 4/1989 | Neurath et al. |
| 4,857,317 A | 8/1989 | Wijnendaele et al. |
| 4,876,241 A | 10/1989 | Feldman et al. |
| 5,114,863 A | 5/1992 | McCombs et al. |
| 5,169,936 A | 12/1992 | Staples et al. |
| 5,276,141 A | 1/1994 | Kolbe |
| 5,610,285 A | 3/1997 | Lebing et al. |
| 5,616,693 A | 4/1997 | Hwang et al. |
| 5,780,014 A | 7/1998 | Eljamal et al. |
| 6,093,804 A | 7/2000 | Ralston et al. |
| 6,096,216 A | 8/2000 | Shanbrom et al. |
| 6,106,773 A | 8/2000 | Miekka et al. |
| 6,138,668 A | 10/2000 | Patton et al. |
| 6,187,572 B1 | 2/2001 | Platz et al. |
| 6,369,048 B1 | 4/2002 | Budowsky et al. |
| 6,436,344 B1 | 8/2002 | Miekka et al. |
| 6,462,180 B1 | 10/2002 | Lebing et al. |
| 6,465,168 B1 | 10/2002 | Castor et al. |
| 6,974,792 B2 | 12/2005 | Mattes et al. |
| 7,777,006 B2 | 8/2010 | Kee et al. |
| 8,124,736 B2 | 2/2012 | Kee et al. |
| 8,722,624 B2 | 5/2014 | Kee et al. |
| 2001/0051154 A1 | 12/2001 | Roemisch et al. |
| 2002/0082214 A1 | 6/2002 | Mattes et al. |

FOREIGN PATENT DOCUMENTS

| | | |
|---|---|---|
| EP | 0 067 293 A2 | 12/1982 |
| EP | 0 067 293 B1 | 6/1986 |

(Continued)

OTHER PUBLICATIONS

Alpha Therapeutic Corporation, "Alpha$_1$-Proteinase Inhibitor (Human) Aralast™ Solvent Detergent Treated Nanofiltered", Product Information, Dec. 2002, 2 pp.

(Continued)

*Primary Examiner* — Robert Yamasaki
(74) *Attorney, Agent, or Firm* — Finnegan, Henderson, Farabow, Garrett & Dunner, LLP

(57) ABSTRACT

A streamlined method for purifying alpha-1-antitrypsin (AAT) from an AAT-containing protein mixture, such as Coh fraction IV precipitate, is provided. In the method of the invention, contaminating proteins are destabilized by cleavage of disulfide bonds with a reducing reagent, such as dithiol, which does not affect AAT. The destabilized proteins are then preferentially adsorbed on a solid protein-adsorbing material, without the addition of a salt as a precipitante. Spearation of the solid absorbent from the solution leaves a purified AAT solution that is directly suitable for chromatographic purification, without the need for extensive desalting as in prior art processes. A process incorporating this method, which provides pharmaceutical grade AAT in high yield on a commercial scale, is also described.

14 Claims, 2 Drawing Sheets

(56) References Cited

FOREIGN PATENT DOCUMENTS

| | | |
|---|---|---|
| EP | 0 244 811 B1 | 8/1990 |
| EP | 0 421 309 A2 | 4/1991 |
| EP | 0 282 363 B1 | 9/1992 |
| EP | 0 288 841 B1 | 12/1992 |
| EP | 0 562 643 A2 | 9/1993 |
| EP | 0 717 049 A1 | 6/1996 |
| EP | 0 717 049 B1 | 4/1998 |
| EP | 0 698 615 B1 | 12/1999 |
| JP | S58-4728 | 1/1983 |
| JP | S59-128335 | 7/1984 |
| JP | S63-309189 | 12/1988 |
| JP | H8-99999 | 4/1996 |
| JP | 2000-514647 | 11/2000 |
| JP | 2002-510294 | 4/2002 |
| WO | WO 95/24428 | 9/1995 |
| WO | WO 95/35306 | 12/1995 |
| WO | WO 98/00154 | 1/1998 |
| WO | WO 98/56821 | 12/1998 |
| WO | WO 2000/017227 | 3/2000 |
| WO | WO 2002/048176 A1 | 6/2002 |
| WO | WO 02/057741 A3 | 7/2002 |
| WO | WO 2004/060528 | 7/2004 |

OTHER PUBLICATIONS

Archibald, A.L., et al., "High-level expression of biologically active human $\alpha_1$-antitrypsin in the milk of transgenic mice", *Proc. Natl. Acad. Sci. USA*, vol. 87, Jul. 1990, pp. 5178-5182.

Asztalos et al., "Distribution of ApoA-I-Containing HDL Subpopulations in Patients with Coronary Heart Disease," *Arteriosclerosis, Thrombosis, and Vascular Biology*, vol. 20, 2000, pp. 2670-2676.

Bischoff, R., et al., "Purification and Biochemical Characterization of Recombinant $\alpha_1$-Antitrypsin Variants Expressed in *Escherichia coli*", *Biochemistry*, vol. 30, 1991, pp. 3464-3472.

Brantly, M., et al., "Molecular Basis of Alpha-1-Antitrypsin Deficiency", *American Journal of Medicine*, vol. 84, Suppl. 6A, Jun. 24, 1988, pp. 13-31.

Buckley, R., "IgA Deficiency: Immunodeficiency Disorders: Merck Manual Professional", Merck, Sharp & Dohme Corp., Sep. 2008, 2 pp.

Burnouf, T., et al., "Biochemical and Biological Properties of an $\alpha_1$-Antitrypsin Concentrate", *Vox Sang.*, vol. 52, 1987, pp. 291-297.

Carrell, R.W., et al., "Structure and variation of human $\alpha_1$-antitrypsin", *Nature*, vol. 298, Jul. 22, 1982, pp. 329-334.

Chen, S.X. et al., "Purification of $\alpha_1$ Proteinase Inhibitor from Human Plasma Fraction IV-1 by Ion Exchange Chromatography," *Vox Sang.* 1998, 74:232-241.

Chen, S.X., et al., "Chromatographic purification of human $\alpha_1$ proteinase inhibitor from dissolved Cohn fraction IV-1 paste", *J. Chromatogr. A*, vol. 800, 1998, pp. 207-218.

Coan, M.H., "Purification of Alpha-1 Proteinase Inhibitor", *American Journal of Medicine*, vol. 84, Suppl. 6A, Jun. 24, 1988, pp. 32-36.

Coan, M.H., et al., "Preparation and Properties of Alpha$_1$-Proteinase Inhibitor Concentrate from Human Plasma", *Vox Sang.*, vol. 48, 1985, pp. 333-342.

Cohn, E.J., et al., "Preparation and Properties of Serum and Plasma Proteins. IV. A System for the Separation into Fractions of the Protein and Lipoprotein Components of Biological Tissues and Fluids", *J. Am. Chem. Soc.*, vol. 68, No. 3, Mar. 1946, pp. 459-475.

Cowden, D.I., et al., "A pilot study comparing the purity, functionality and isoform composition of alpha-1-proteinase inhibitor (human) products", *Current Medical Research and Opinion*, vol. 21, No. 6, Jun. 2005, pp. 877-883.

CSL Behring Memo re: Purification of alpha-1 proteinase inhibitor using the method defined by Erwin Mattes et al. (Baxter Hyland Immuno) published in Vox Sanguinis 81, 29-36 (2001); dated Mar. 26, 2015 (5 pages).

Dubin, A., et al., "Isolation of Nine Human Plasma Proteinase Inhibitors by Sequential Activity Chromatography", *Prep. Biochem.*, vol. 20, No. 1, 1990, pp. 63-74.

European Patent Office communication, Office Action in European Patent Application No. 10182334.2, dated Dec. 5, 2014, 3 pages.

Examination Report Action dated Nov. 14, 2011 issued in European Application No. 10182334.2.

Examination Report dated Dec. 4, 2008 issued in European Application No. 03814875.5.

Examiner's Report dated Aug. 7, 2008 issued in Australian Application No. 2003301108.

Extended Search Report dated Feb. 11, 2011 issued in European Application No. 10182334.2.

Gaidulis, L., et al., "Optimizing Reference Values for the Measurement of Alpha$_1$-Antitrypsin in Serum: Comparison of Three Methods", *Clin. Chem.*, vol. 29, No. 10, 1983, pp. 1838-1840.

Glaser, C.B., et al., "Isolation and Characterization of Alpha-1-Antitrypsin from the Cohn Faction IV-I of Human Plasma", *Prep. Biochem.*, vol. 5, No. 4, 1975, pp. 333-348.

Glaser, C.B., et al., "The Isolation of Alpha-1-Protease Inhibitor by a Unique Procedure Designed for Industrial Application", *Analytical Biochemistry*, vol. 124, 1982, pp. 364-371.

Hansson and Johnsson et al., "Improved Technique for Detecting Australia Antigen by Immunoelectroosmophoresis," *Vox Sang*, vol. 21, 1971, pp. 531-539.

Hao, Y.L., et al., "An Integrated Plasma Fractionation System Based on Use of Polyethylene Glycol", Proceedings of the International Workshop on Technology for Protein Separation and Improvement of Blood Plasma Fractionation, National Institutes of Health, Sep. 1977, pp. 372-379.

Hein, R.H., et al., "Production of alpha$_1$-proteinase inhibitor (human)", *Eur. Respir. J.*, vol. 3, Suppl. 9, 1990, pp. 16s-20s.

Huang, J., et al., "Expression and Purification of Functional Human $\alpha_1$-Antitrypsin from Cultured Plant Cells", *Biotechnol. Prog.*, vol. 17, 2001, pp. 126-133.

International Search Report dated Apr. 27, 2004 issued in Application No. PCT/US2003/040560.

Karathanasis et al., "Isolation and characterization of the human apolipoprotein A-I gene," *Proc. Natl. Acad. Sci. USA*, vol. 80, 1983, pp. 6147-6151.

Karnaukhova et al., "Recombinant human alpha-1 proteinase inhibitor: towards therapeutic use," *Amino Acids*, vol. 30, 2006, pp. 317-332.

Kistler, P., et al., "Large Scale Production of Human Plasma Fractions", *Vox Sang.*, vol. 7, 1962, pp. 414-424.

Kolarich, D., et al., "Biochemical, molecular characterization, and glycoproteomic analyses of $\alpha_1$-proteinase inhibitor products used for replacement therapy," *Transfusion*, 46: 1959-1977 (2006).

Kress, L.F., et al., "Large Scale Purification of Alpha-1 Trypsin Inhibitor from Human Plasma", *Prep. Biochem.*, vol. 3, No. 6, 1973, pp. 541-552.

Kwon, K-S, et al., "Purification and characterization of $\alpha_1$-antitrypsin secreted by recombinant yeast *Saccharomyces diastaticus*", *J. Biotechnol.*, vol. 42, 1995, pp. 191-195.

Laurell, C.B., et al., "The Use of Thiol-Disulphide Exchange Chromatography for the Automated Isolation of $\alpha_1$-Antitrypsin and Other Plasma Proteins with Reactive Thiol Groups", *J. Chromatogr.*, vol. 278, 1983, pp. 53-61.

Lodish, H.F., et al., "The Secretory Pathway Is Normal in Dithiothreitol-treated Cells, But Disulfide-bonded Proteins Are Reduced and Reversibly Retained in the Endoplasmic Reticulum", *J. Biol. Chem.*, vol. 268, No. 27, Sep. 25, 1993, pp. 20598-20605.

Lomas, D.A., et al., "Commercial plasma $\alpha_1$-antitrypsin (Prolastin®) contains a conformationally inactive, latent component", *Eur. Respir. J.*, vol. 10, 1997, pp. 672-675.

Mahadeva, R., et al., "Alpha$_1$-antitrypsin deficiency, cirrhosis and emphysema", *Thorax*, vol. 53, 1998, pp. 501-505.

Mattes, E., et al., "Preparation and properties of an alpha-1-protease inhibitor concentrate with high specific activity", *Vox Sang.*, vol. 81, 2001, pp. 29-36.

Mitra, G., et al., "Inactivation of Viruses in Therapeutic Products Derived from Human Plasma", *American Journal of Medicine*, vol. 84, Suppl. 6A, Jun. 24, 1988, pp. 87-90.

(56) References Cited

OTHER PUBLICATIONS

Office Action dated Oct. 28, 2010, issued in Canadian Application No. 2,511,986.
Official Action (English summary only) dated Sep. 11, 2009 issued in Japanese Application No. 2004-565589.
Official Interrogatory (English summary only) dated Mar. 15, 2012 issued in Japanese Application No. 2004-565589.
Oláh, S., et al., "Hydrophobic interaction chromatography of human serum $\alpha_1$-antitrypsin and $\alpha_1$-acid glycoprotein", *J. Chromatogr. B*, vol. 744, 2000, pp. 73-79.
Pannell, R., et al., "Isolation and Properties of Human Plasma $\alpha$-1-Proteinase Inhibitor", *Biochemistry*, vol. 13, No. 26, 1974, pp. 5439-5445.
Patent Examination Report No. 2 dated Mar. 26, 2014 for Australian Application No. 2012203030.
Podiarene, S.M., et al., English-language abstract only for Russian-language article "Immunoaffinity purification of alpha 1 protease inhibitor from human plasma" (Vopr. Med. Khim., vol. 35, No. 5, Sep. Oct. 1989, pp. 96 99), 1 pg.
Reply to Examination Report in European Patent Application No. 10182334.2-1401 dated Apr. 15, 2015 (8 pages).
Rezaee et al., "Proteomic analysis of high-density lipoprotein," *Proteomics*, vol. 6, 2006, pp. 721-730.
Rye et al., "Remodelling of high density lipoproteins by plasma factors," *Atherosclerosis*, vol. 145, 1999, pp. 227-238.
Stephan, W., "Hepatitis-Free and Stable Human Serum for Intravenous Therapy", *Vox Sang.*, vol. 20, 1971, pp. 442-457.
Supplementary Partial Search Report dated Jan. 10, 2006 issued in European Application No. 03814875.
Supplementary Partial Search Report dated Jun. 26, 2006 issued in European Application No. 03814875.
Supplementary Search Report dated Jul. 6, 2006, issued in European Application No. 03814875.5.
Svoboda, M., et al., "Purification of Somatomedin-C/Insulin-Like Growth Factor I", *Methods Enzymol.*, vol. 109, 1985, pp. 798-816.
The Alpha-1-Antitrypsin Deficiency Registry Study Group, "Survival and $FEV_1$ Decline in Individuals with Severe Deficiency of $\alpha_1$-Antitrypsin", *Am. J. Respir. Crit. Care Med.*, vol. 158, 1998, pp. 49-59.
Von Zychlinski and Kleffmann, "Dissecting the proteome of lipoproteins: New biomarkers for cardiovascular disease?" *Translational Proteomics*, vol. 7, 2015, pp. 30-39.
Whicher, J.T., et al., "New International Reference Preparation for Proteins in Human Serum (RPPHS)", *Clin. Chem.*, vol. 40, No. 6, 1994, pp. 934-938.
Wright, G., et al., "High Level Expression of Active Human Alpha-1-Antitrypsin in the Milk of Transgenice Sheep", *Biotechnology*, vol. 9, Sep. 1991, pp. 830-834.
A1PI Purification according to the descriptions in Chen et al., "Chromatographic purification of human $\alpha$1 proteinase inhibitor from dissolved Cohn fraction IV-1 paste," Journal of Chromatography, 1998; 800: 207-218, and Laurell et al., "The use of thiol-disulphide exchange chromatography for the automated isolation of $\alpha_1$-antitrypsin and other plasma proteins with reactive thiol groups," Journal of Chromatography, 1983; 278: 53-61; submitted in Opposition of European Patent No. EP2295126, Sep. 16, 2016 (7 pages).
A1PI purification according to the description in Glaser et al., "The Isolation of Alpha-1-Protease Inhibitor by a Unique Procedure Designed for Industrial Application," Analytical Biochemistry, 1982; 124: 364-371; submitted in Opposition of European Patent No. EP2295126, Sep. 16, 2016 (7 pages).
Brantly, M. L. et al., "Use of a Highly Purified $\alpha_1$-Antitrypsin Standard to Establish Ranges for the Common Normal and Deficient $\alpha_1$-Antitrypsin Phenotypes," Chest, 1992; 100(3): pp. 703-708.
Cunningham-Rundles, C. et al., "Use of an IgA-Depleted Intravenous Immunoglobulin in a Patient with an Anti-Iga Antibody," Clinical Immunology and Immunopathology, 1986; 38: pp. 141-149.
Doellgast, G. J. et al., "Purification of Human IgA by Salt-Mediated Hydrophobic Chromatography," Immunochemistry, 1976, vol. 13, pp. 135-139.
Purification of alpha-1 antitrypsin (AAT) using the process disclosed in WO 02/48176; submitted in Opposition of European Patent No. EP2295126, Sep. 15, 2016 (4 pages).
Flowchart of combined purification protocols of Chen et al., "Chromatographic purification of human $\alpha$1 proteinase inhibitor from dissolved Cohn fraction IV-1 paste," Journal of Chromatography, 1998; 800: 207-218, and Laurell et al., "The use of thiol-disulphide exchange chromatography for the automated isolation of $\alpha$1-antitrypsin and other plasma proteins with reactive thiol groups," Journal of Chromatography, 1983; 278: 53-61; submitted in Opposition of European Patent No. EP2295126, Sep. 16, 2016 (1 page).
Lilic, D. et al., "IgA deficiency: what we should-or should not-be doing," J. Clin. Pathol, 2001; 54: 337-338.
Lopez, M. F., "A comparison of silver strain and SYPRO Ruby Protein Gel Stain with respect to protein detection in two-dimensional gels and identification by peptide mass profiling," Electrophoresis, 2000; 21: pp. 3673-3683.
Miller, W. V. et al., "Anaphylactic Reactions to IgA: A Difficult Transfusion Problem," American Journal of Clinical Pathology, 1970; 54(4): pp. 618-621.
Miller, I. et al., "Protein stains for proteomic applications: *Which, when, why?*" Protemics, 2006; 6: pp. 5385-5408.
Nilson, B. H.K. et al., "Purification of antibodies using protein L-binding framework structures in the light chain variable domain," Journal of Immunological Methods, 1993; 164: pp. 33-40.
Notice of Opposition to European Patent No. EP2295126, filed by Octapharma AG on Sep. 16, 2016 (35 pages).
Notice of Opposition to European Patent No. EP2295126, filed by Furo Ventures B.V. on Sep. 16, 2016 (10 pages).
Notice of Opposition to European Patent No. EP2295126, filed by J.G. Leeming on Sep. 15, 2016 (23 pages).
Pellicon Tangential Flow Filtration Cassettes, Advertising Material, Millipore, copyright 1999 (8 pages).
U.S. Appl. No. 10/334,303, filed Dec. 31, 2002, dated Mar. 2, 2004 (50 pages).
Summary Basis for Approval, Proprietary Name: Zemaire™ (37 pages) (redacted).
Trizma® Buffers—Product Specification, Sigma-Aldrich Co., copyright 1996 (2 pages).
Wan, Y. et al., "High-resolution plasma protein fractionation using ultrafiltration," Desalination, 2002; 144: pp. 301-306.

METHODS OF TREATMENT USING ALPHA-1-ANTITRYPSIN COMPOSITIONS

CROSS-REFERENCES TO RELATED APPLICATIONS

This application is a continuation of U.S. patent application Ser. No. 14/805,885, filed Jul. 17, 2015, which is a continuation of U.S. patent application Ser. No. 14/223,010, filed Mar. 24, 2014, which a continuation of U.S. patent application Ser. No. 13/385,642, filed Feb. 28, 2012, now U.S. Pat. No. 8,722,624, which is a continuation of U.S. patent application Ser. No. 12/855,721, filed Aug. 13, 2010, now U.S. Pat. No. 8,124,736, which is a divisional of U.S. application Ser. No. 10/334,303, filed Dec. 31, 2002, now U.S. Pat. No. 7,777,006. In addition, International Application No. PCT/US03/40560, filed Dec. 19, 2003, claims the benefit of U.S. application Ser. No. 10/334,303, filed Dec. 31, 2002, now U.S. Pat. No. 7,777,006. All of these prior applications are incorporated herein by reference.

BACKGROUND

The invention relates to protein separation and purification methods. More specifically, the invention relates to the separation of alpha-1-antitrypsin (AAT, also known as alpha-1 proteinase inhibitor, API, and $A_1$-PI) from complex protein mixtures such as blood plasma fractions, and to methods for further purification of the separated AAT so as to provide a composition suitable for pharmaceutical use.

Alpha-I-antitrypsin (AAT) is a glycopeptide inhibitor of proteases, and is found in human serum and other fluids. Protease inhibition by AAT is an essential component of the regulation of tissue proteolysis, and AAT deficiency is implicated in the pathology of several diseases. Individuals who inherit an alpha-1-antitrypsin deficiency, for example, have increased risk of suffering from severe early-onset emphysema, the result of unregulated destruction of lung tissue by human leukocyte elastase. The administration of exogenous human AAT has been shown to inhibit elastase and is associated with improved survival and reduction in the rate of decline of lung function in AAT-deficient patients (Crystal et al., *Am. J Respir. Crit. Care Med.* 158:49-59 (1998); see R. Mahadeva and D. Lomas, *Thorax* 53:501-505 (1998) for a review.)

Because of its therapeutic utility, commercial AAT production has been the subject of considerable research. Much progress has been made in the production of recombinant AAT in *E. coli* (R. Bischoff et al., *Biochemistry* 30:3464-3472 (1991)), yeast (K. Kwon et al., *J. Biotechnology* 42:191-195 (1995); Bollen et al., U.S. Pat. No. 4,629,567), and plants (J. Huang et al., *Biotechnol. Prog.* 17:126-33 (2001)), and by secretion in the milk of transgenic mammals (G. Wright et al., *Biotechnology,* 9:830-834 (1991); A. L. Archibald, *Proc. Natl. Acad. Sci. USA,* 87:5178-5182 (1990)). However, isolation of AAT from human plasma is presently the most efficient practical method of obtaining AAT in quantity, and human plasma is the only FDA-approved source.

A number of processes for isolating and purifying AAT from human plasma fractions have been described, involving combinations of precipitation, adsorption, extraction, and chromatographic steps. In order to minimize the risk of pathogen transfer, pooled human plasma intended for production of human AAT for therapeutic use is screened for the hepatitis B surface antigen, and for antibodies to the human immunodeficiency virus. As an additional precaution against transmission of infectious agents, the purified product is ordinarily pasteurized by heating to 60° C. for 10 hours (Mitra et al., *Am. J. Med.* 84(sup. 6A):87-90 (1988)) and sterile filtered.

Most published processes for AAT isolation begin with one or more fractions of human plasma known as the Cohn fraction IV precipitates, e.g. Cohn fraction $IV_1$ or fraction $IV_{1-4}$, which are obtained from plasma as a paste after a series of ethanol precipitations and pH adjustments (E. J. Cohn et al., *J. Amer. Chem. Soc.,* 68:459-475 (1946)).

U.S. Pat. No. 3,301,842 describes a method for isolation of AAT from Cohn fraction $IV_1$ wherein an acridine or quinoline derivative is added to the paste in a buffer at pH 6, the precipitate is discarded, and the pH adjusted to 7.0. Additional acridine or quinoline is added, and the precipitate is collected. This precipitate is dissolved in a pH 5.0 buffer, sodium chloride is added, and the resulting precipitate discarded. The solution, containing the AAT, is further processed by methanol precipitation. Alternatively, ammonium sulfate precipitations at pH 8 and at pH 5 are conducted with plasma, with the pH 5 supernatant being farther processed as above with quinoline or acridine additives.

Glaser et al., *Preparative Biochemistry,* 5:333-348 (1975), disclosed a method for isolating AAT from Cohn fraction $IV_1$ paste. The paste is stirred in a phosphate buffer at pH 8.5 in order to reactivate the AAT, which is largely deactivated by the pH of 5.2 employed in the Cohn fractionation. After dialysis and centrifugation, the supernatant is subjected to two rounds of anion exchange chromatography at pH 6.0 to 7.6 and at pH 8.6, followed by further chromatographic processing at pH 7.6 and at pH 8.0, to produce AAT in about a 30% overall yield.

M. H. Coan et al., in U.S. Pat. Nos. 4,379,087 and 4,439,358 (see also M. H. Coan et al., *Vox Sang.,* 48:333-342 (1985); M. H. Coan, *Amer. J. Med.,* 84(sup 6A):32-36 (1988); and R. H. Hein et al., *Eur. Respir. J.,* 3(sup 9):16s-20s (1990)), disclosed a procedure wherein Cohn fraction $IV_1$ paste is dissolved in a pH 6.5 to 8.5 buffer, polyethylene glycol is added, and the pH is lowered to the range of 4.6 to 5.7 to precipitate unwanted proteins. After centrifugation, AAT is isolated from the supernatant by anion exchange chromatography. Further processing provides a 45% yield of AAT with a purity of about 60%. Methods employing polyethylene glycol as a precipitant are also described in U.S. Pat. Nos. 4,697,003, 4,656,254, and Japanese patent JP 08099999, described below; and also by Hao et al., *Proc. Intl. Workshop on Technology for Protein Separation and Improvement of Blood Plasma Fractionation,* Sep. 7-9, 1977, Reston, Va.

Dubin et al., *Preparative Biochemistry.* 20:63-70 (1990), disclosed a two step chromatographic purification, in which AAT was first eluted from Blue SEPHAROSE® and then purified by gel filtration chromatography.

Schultze and Heimburger, in U.S. Pat. No. 3,293,236, disclosed purification of AAT using cation exchange chromatography with a citrate buffer, in combination with ammonium sulfate fractionation of human plasma.

Lebing and Chen, in U.S. Pat. No. 5,610,285, disclosed a purification process which employs an initial anion exchange chromatography, followed by cation exchange chromatography at low pH and low ionic strength, to purify human AAT from plasma and plasma fractions. The cation chromatography takes advantage of the fact that active AAT does not bind to the ion exchange column under these conditions while contaminating proteins, including denatured AAT and albumin, are retained.

Jordan et al., in U.S. Pat. No. 4,749,783, described the isolation of AAT from human plasma using affinity chromatography with monoclonal antibodies. See also Podiarene et al., *Vopr. Med. Khim.* 35:96-99 (1989).

Shearer et al., in European patent application EP 0 224 811 and in the corresponding U.S. Pat. No. 4,656,254, disclosed an improved method for extracting AAT from Cohn fraction IV paste, in which the improvement consisted of treating the paste with a larger volume of buffer, at a higher pH, than had been customary in the prior art. The combination of higher volume and higher pH increased the amount of AAT extracted from the paste. Unwanted proteins were precipitated by addition of polyethylene glycol, followed by centrifugation. An alternative procedure is disclosed, which is essentially the procedure of Coan et al., wherein after addition of polyethylene glycol, the pH is adjusted to the range of 4.6 to 5.7, and the acidified mixture held for from one to sixty minutes to further precipitate unwanted proteins. The AAT is precipitated by addition of additional polyethylene glycol, and further purified by anion exchange chromatography.

Arrighi et al., in European application EP 0717049, disclosed a process wherein fraction $IV_1$ paste is stirred in a pH 8.2 buffer at 40° C. for one hour, followed by precipitation of unwanted proteins with ammonium sulfate. The AAT is isolated from the supernatant by hydrophobic interaction chromatography at pH 7.

Kress et al., in *Preparative Biochemistry* 3:541-552 (1973), dialyzed the precipitate from an 80% ammonium sulfate treatment of human plasma, then chromatographed it on DEAE-cellulose. The product was dialyzed again and gel filtered on SEPHADEX™ G-100. AAT-containing fractions were then chromatographed on DE-52 cellulose to give AAT.

Japanese patent 59-128335 discloses the precipitation of unwanted proteins from a plasma fraction by addition of polyethylene glycol at a pH between 5 and 7, followed by anion exchange chromatography.

Bollen et al., in U.S. Pat. No. 4,629,567, disclose the isolation of AAT from a culture of yeast carrying recombinant plasmids expressing AAT. The process begins with polyethylene glycol precipitation at pH 6.5 to remove contaminating proteins, followed by anion exchange chromatography at pH 6.5 and subsequent chromatographic steps.

Dove and Mitra, in U.S. Pat. No. 4,684,723, disclose a variant of the method of Coan et al. (U.S. Pat. Nos. 4,379, 087 and 4,439,358) in which AAT is purified by a process comprising the steps of (a) holding a solution containing AAT at a pH of 6.5 to 8.5 for up to 24 hours, (b) adding polyethylene glycol and an inorganic salt, so as to obtain a two-phase mixture, and (c) isolating the aqueous salt phase, which contains purified AAT.

Taniguchi et al., in PCT application WO 95/35306, disclose a similar process, involving precipitation with polyethylene glycol in the presence of zinc chloride, followed by anion-exchange chromatography and chromatography on a metal chelate resin.

Van Wietnendaele et al., in U.S. Pat. No. 4,857,317, also disclose a process for isolating AAT from the crude extract of an engineered yeast culture, which comprises addition of polyethylene glycol at pH 6.1, centrifugation to remove precipitated proteins, addition of calcium chloride, storage for 24 hours at pH 7.0, and centrifugation to further remove contaminants. AAT is then isolated from the supernatant by subsequent chromatographic steps.

Coan, in U.S. Pat. No. 4,697,003, discloses a method for isolating AAT from various Cohn plasma fractions which comprises the removal of ethanol and salts from an AAT-containing fraction, followed by anion-exchange chromatography on DEAE cellulose or a similar material under conditions such that the AAT is retained on the column while undesired proteins are eluted. Coan also describes "pasteurization" at about 60° C. or more for about 10 hours, which is stated to be sufficient to render hepatitis viruses non-infective.

Coan discloses addition of carbohydrate as a stabilization agent, either alone or with sodium citrate, in order to stabilize the AAT at the pasteurization temperature. Suitable carbohydrates are said to be mono-, di-, and trisaccharides, and sugar alcohols such as sorbitol and mannitol. AAT is prone to both polymerization and to the adoption of inactive conformations upon heating; the presence of stabilizers reduces but does not eliminate thermal inactivation (D. Lomas et al., *Eur. Resp. J.* 10:672-675 (1997)). Size-exclusion HPLC analysis has shown that 10% of monomeric AAT is polymerized or aggregated when pasteurization is carried out according to the Coan process (M. H. Coan et al., *Vox Sang.*, 48:333-342 (1985)).

T. Burnouf et al., *Vox Sang.*, 52:291-297 (1987), disclosed substantially the same procedure for isolating AAT from Kistler-Nitschmann supernatant A. DEAE chromatography of Cohn Fractions II+III and size exclusion chromatography produced an AAT which was 80-90% pure (by SDS-PAGE) with a 36-fold increase in purity. Recovery was 65-70%.

Thierry, in European patent application EP 0282363, also discloses a method of obtaining AAT from a Kistler-Nitschmann plasma fraction. Briefly, plasma is precipitated with 10% ethanol at pH 7.4, and the supernatant precipitated again with 19% ethanol at pH 5.85. The supernatant from the second precipitation is applied to a DEAE anion-exchange column, and eluted at pH 5.2 to provide AAT of about 90% purity.

Strancar et al., in PCT patent application WO 95/24428, disclose a very similar method, employing a particular class of functionalized anion-exchange media. Desalted Cohn fraction $IV_1$ is applied to the column, and contaminating proteins are eluted with low salt buffer at a pH "close to the pKa of acetic acid." (The pKa of acetic acid is 4.74.) AAT is then eluted with 50 to 300 mM NaCl at pH 7.4 to 9.2.

Japanese patent JP 08099999 discloses a method of obtaining AAT from Cohn fraction IV or $IV_1$, which involves reduction of salt concentration to below about 0.02 M, adjusting the pH to 4.5 to 5.5, and contacting the solution with a cation exchanger to adsorb contaminating proteins.

M. E. Svoboda and J. J. van Wyk, in *Meth. Enzymology*, 109:798-816 (1985), disclose acid extraction of Cohn fraction IV paste with phosphoric, formic, and acetic acids.

Glaser et al., in *Anal. Biochem.*, 124:364-371 (1982) and also in European Patent Application EP 0 067 293, disclose several variations on a method for isolating AAT from Cohn fraction $IV_1$ precipitate which comprises the steps of (a) dissolving the paste in a pH 8.5 buffer, (b) filtering, (c) adding a dithiol such as DTT, and (d) precipitation of denatured proteins with ammonium sulfate. Glaser states that the destabilized (DTT-reduced) proteins may be precipitated by "suitable techniques such as salting, heating, change in pH, addition of solvents and the like."

Glaser et al. describe one variation in which treatment with DTT is carried out in the presence of 2.5% AEROSIL® fumed silica, prior to precipitation with 50% saturated ammonium sulfate. Recovery of AAT was as good as it was in the absence of the silica, and the purification factor was improved by about 70%. In both references, the authors relegate the silica to a secondary role, that of an additive that improves the results of the ammonium sulfate precipitation. The effectiveness of silica alone, without ammonium sulfate precipitation, is not recognized or described. If the concentration of the protein solution appreciably exceeds about 50 mg protein/ml, AAT is reportedly lost by occlusion in the precipitate.

Ralston and Drohan, in U.S. Pat. No. 6,093,804, disclose a method involving the removal of lipoproteins from an initial protein suspension via a "lipid removal agent," followed by removal of "inactive AAT" via elution from an anion-exchange medium with a citrate buffer. The lipid removal agent is stated to be MICRO CEL® E, a synthetic hydrous calcium silicate. In the presence of a non-citrate buffer, the anion-exchange medium binds active AAT while allowing "inactive AAT" to pass through. A citrate buffer is specified for subsequent elution of the AAT from the anion exchange medium, and also for later elution from a cation-exchange medium. Ralston and Drohan do not describe the use of a disulfide-reducing agent. The process is stated to provide AAT with a product purity of >90%; and manufacturing scale yields of >70%.

W. Stephan, in *Vox Sanguinis* 20:442-457 (1971), describes the use of fumed silica to adsorb lipoproteins from human blood serum solutions. The effect of silica adsorption on the concentrations of several plasma proteins, including AAT, was evaluated, and there was no significant loss of AAT.

Mattes et al., in *Vox Sanguinis* 81:29-36 (2001), and in PCT application WO 98/56821 and published US patent application 2002/0082214, disclose a method for isolating AAT from Cohn fraction IV which involves ethanol precipitation, anion exchange chromatography, and adsorption chromatography on hydroxyapatite. The latter step is reported to remove inactive AAT, providing a product with very high specific activity.

While AAT is an effective treatment for emphysema due to alpha-1-antitrypsin deficiency, treatment is very costly (currently about $25,000 per year), due to the limited supply and a complex manufacturing process. There remains a need for more efficient and cost-effective methods for isolating human AAT from plasma and other complex protein mixtures containing AAT. In particular, ammonium sulfate precipitation followed by dialysis is a time-consuming process, that generates substantial amounts of waste water, and there is a need for scalable processes that do not require extensive dialysis while providing high yields of high activity, high purity AAT. Thermal pasteurization of AAT effectively reduces viral contamination, but it leads to the formation of inactive AAT aggregates and polymers. Thus, there is also a need for highly pure AAT with reduced viral contamination but without significant amounts of inactive AAT aggregates and polymers. The present invention addresses these needs.

BRIEF SUMMARY

The invention provides a method for purifying AAT from crude AAT-containing protein precipitates, which consists essentially of the following steps: (a) suspending the AAT-containing protein mixture in a buffer under conditions that permit the AAT to be dissolved; (b) contacting the resulting suspension with a disulfide-reducing agent to produce a reduced suspension; (c) contacting the reduced suspension with an insoluble protein-adsorbing material; and (d) removing insoluble materials from the suspension. This process provides an enriched AAT preparation, directly suitable for chromatographic processing, with reduced costs and in less time than prior art processes. Additional purification steps may be performed at the discretion of the practitioner, as described further below.

More specifically, the process comprises the steps of: (a) suspending a crude AAT-containing protein precipitate in a buffer under conditions that permit the AAT to be dissolved; (b) contacting the resulting suspension with a disulfide-reducing agent, under conditions that permit reduction of intra-protein disulfide bonds by the reducing agent, to produce a reduced suspension; (c) contacting the reduced suspension with an insoluble protein-adsorbing material, without the addition of a substantial amount of additional salts and (d) removing insoluble materials from the suspension, so as to obtain a clarified protein solution.

By "substantial amount of additional salts" is meant an amount of soluble salt or salts that will cause otherwise-soluble proteins to begin precipitating from the solution in significant amounts. Those salts ordinarily used to cause any degree of protein precipitation, in the amounts ordinarily used for such purposes, are specifically included.

The method of the invention eliminates the salting-out step which was taught by Glaser in EP 0 067 293, which in turn avoids the time and cost associated with the need to desalt the filtrate by extensive dialysis. Furthermore, the ammonium sulfate precipitation employed by Glaser limited the concentration of the protein solutions that could be processed. If the protein concentration appreciably exceeds about 50 mg/ml in Glaser's method, AAT is reportedly lost by occlusion in the AEROSIL®/protein precipitate. In the absence of ammonium sulfate, higher concentrations of protein should be usable without precipitation and occlusion of AAT, with associated savings in reagents and processing time, and greater throughput per batch. The process of the present invention involves two steps where protein concentration exceeds 100 mg/ml in the absence of ammonium sulfate, and no precipitation of AAT has been seen.

The combination of a disulfide-reducing agent and an insoluble protein-adsorbing material according to the invention is particularly effective at removing albumin and transferrin, which are the major protein impurities in serum-derived crude AAT preparations such as Cohn fraction IV precipitates. After removal of the protein-adsorbing material by filtration, both albumin and transferrin levels are below the detection limits of nephelometry when conducted as described herein. Further processing as described herein provides AAT with an average purity of 98% by SDS-PAGE (reduced), and high specific activity, averaging 1.06 mg functional AAT/mg. Compositions with purity greater than 99% by SDS-PAGE, and having specific activities up to 1.12 mg functional AAT/mg protein, can be obtained by the methods disclosed herein.

The crude AAT-containing protein precipitate may be derived from various sources, including but not limited to human serum, serum from a transgenic mammal that expresses human AAT, or milk from a transgenic mammal that secretes human AAT in its milk. The source is preferably serum. If the source is serum, the precipitate is preferably a Cohn fraction IV precipitate, more preferably Cohn fraction IV$_1$, and most preferably Cohn fraction IV$_{1-4}$. There are variations, known to those of skill in the art, in the method for preparing Cohn fractions, and any of them may be employed in the present invention.

The suspension buffer may be any aqueous buffer in which AAT is soluble, and is used in a volume sufficient to dissolve most or all of the AAT present in the precipitate. The preferred volume for suspension of Cohn fraction IV$_{1-4}$ is between 6 and 10 liters per kg of precipitate paste.

Examples of buffers include, but are not limited to, citrate, phosphate, and Tris buffers. The preferred buffer is Tris, preferably 100 mM Tris with 20 mM NaCl. The preferred pH is between 8.80 and 8.95.

The disulfide-reducing agent may be any dithiol commonly used to reduce disulfide bonds in proteins; including but not limited to dithiothreitol (DTT), dithioerythritol (DTE), 1,2-ethanedithiol, 1,2-propanedithiol, 1,3-propanedithiol, and the like; or a phosphine such as tributylphosphine or trimethylphosphine. The disulfide-reducing agent is preferably a dithiol, and most preferably dithiothreitol.

The insoluble protein-adsorbing material may be any of various known adsorbents for hydrophobic proteins, such as fumed silica; silica hydrogels, xerogels, and aerogels; calcium, aluminum and magnesium silicates; certain clays or minerals; and mixtures thereof. Such materials are commonly used for the clarification of food oils and beverages, and are well-known to those of skill in the art. Preferably the protein-adsorbing material is a silica adsorbent, more preferably a fumed silica such as that sold under the trade name AEROSIL®.

The invention also provides a novel combination of purification and virus reduction and inactivation steps, which produces a high-safety and high-purity AAT suitable for pharmaceutical use. Specifically, while the use of dithiothreitol and fumed silica in AAT purification processes has been described previously, the combination of the two in the absence of high temperatures or a precipitating agent such as ammonium sulfate has not been described previously. Surprisingly, it has been found that the omission of a precipitating agent from a dithiothreitol—AEROSIL® treatment step provides a highly effective purification stage. Furthermore, while the uses of dithiothreitol, AEROSIL®, anion exchange chromatography, hydrophobic interaction chromatography, pasteurization, and nanofiltration have each been previously described in the literature, these particular steps are now combined for the first time in a purification process suitable for industrial manufacture of pharmaceutical grade AAT.

The present invention provides a preparation of AAT characterized by the following properties:

(a) the alpha-1-antitrypsin contains less than 6%, preferably less than 2%, and most preferably less than 1% contaminating proteins by SDS-PAGE, and contains (b) less than 0.1% Albumin;

(c) less than 0.8%, and preferably less than or equal to 0.2% $\alpha_1$-acid glycoprotein;

(d) less than 0.1% $\alpha_2$-macroglobulin;

(e) less than 0.1% apolipoprotein AI;

(f) less than 0.5%, and preferably less than or equal to 0.1% antithrombin III;

(g) less than 0.1% ceruloplasmin;

(h) less than 0.5%, and preferably less than 0.1% haptoglobin;

(i) less than 0.2%, and preferably less than 0.1% IgA;

(j) less than 0.1% IgG;

(k) less than 0.1%. transferrin;

(l) the specific activity of the alpha-1-antitrypsin is at least 0.99 mg functional AAT/mg, when using as an extinction coefficient $\Sigma_{1cm,280nm}^{1\%}=5.3$;

(m) less than 8%, and preferably less than 5%, of the product is of a higher molecular weight than monomeric AAT;

(n) the apparent ratio of active to antigenic AAT is greater than 1.08, preferably greater than 1.16, and most preferably greater than 1.23, when measured by endpoint nephelometry;

(o) enveloped viruses are reduced by at least 11 $\log_{10}$ units, and non-enveloped viruses by at least 6 $\log_{10}$ units, when measured in spiking studies using human and model viruses representing a wide range of physico-chemical properties; and (p) the product is stable for at least 2 years when stored lyophilized at up to 25° C.

The apparent ratio of active to antigenic AAT in the product of the present invention is greater than unity because the purity and/or activity of the product of the present invention is greater than that of the reference standard, which is a prior art composition. Antigenic levels, as determined by endpoint nephelometry, are measured against the current protein standard (product No. OQIM15, supplied by Dade-Behring, Deerfield, Ill.), which is calibrated directly against the internationally-recognized Certified Reference Material 470 (Reference Preparation for Proteins in Human Serum; see J T. Whicher et al., *Clin. Chem.* 40:934-938 (1994)), using reagents and AAT antibody (Dade-Behring product No. OSAZ15), as supplied for the Dade-Behring Nephelometer 100.

All publications and patent applications specifically referenced herein are incorporated by reference in their entirety. Unless defined otherwise, all technical and scientific terms used herein have the same meaning as commonly understood by one of ordinary skill in the art to which this invention belongs. The term "AAT" refers to human AAT generally, whether heterogeneous or homogeneous, and whether isolated from human serum or from a recombinant organism. The term is intended to embrace pharmacologically effective naturally-occurring variants (see for example, Brantly et al., *Am. J. Med.* 84(sup.6A):13-31 (1988)), as well as pharmacologically effective non-natural forms of human AAT, including but not limited to those having non-human glycosylation patterns, N-terminal methionine, or altered amino acids. Those of skill in the art will appreciate that methods and materials similar or equivalent to those described herein can be used in the practice of the present invention, and such equivalents are anticipated to be within the scope of the invention. The preferred embodiments described below are provided by way of example only, and the scope of the invention is not limited to the particular embodiments described.

DETAILED DESCRIPTION

Figure 1:
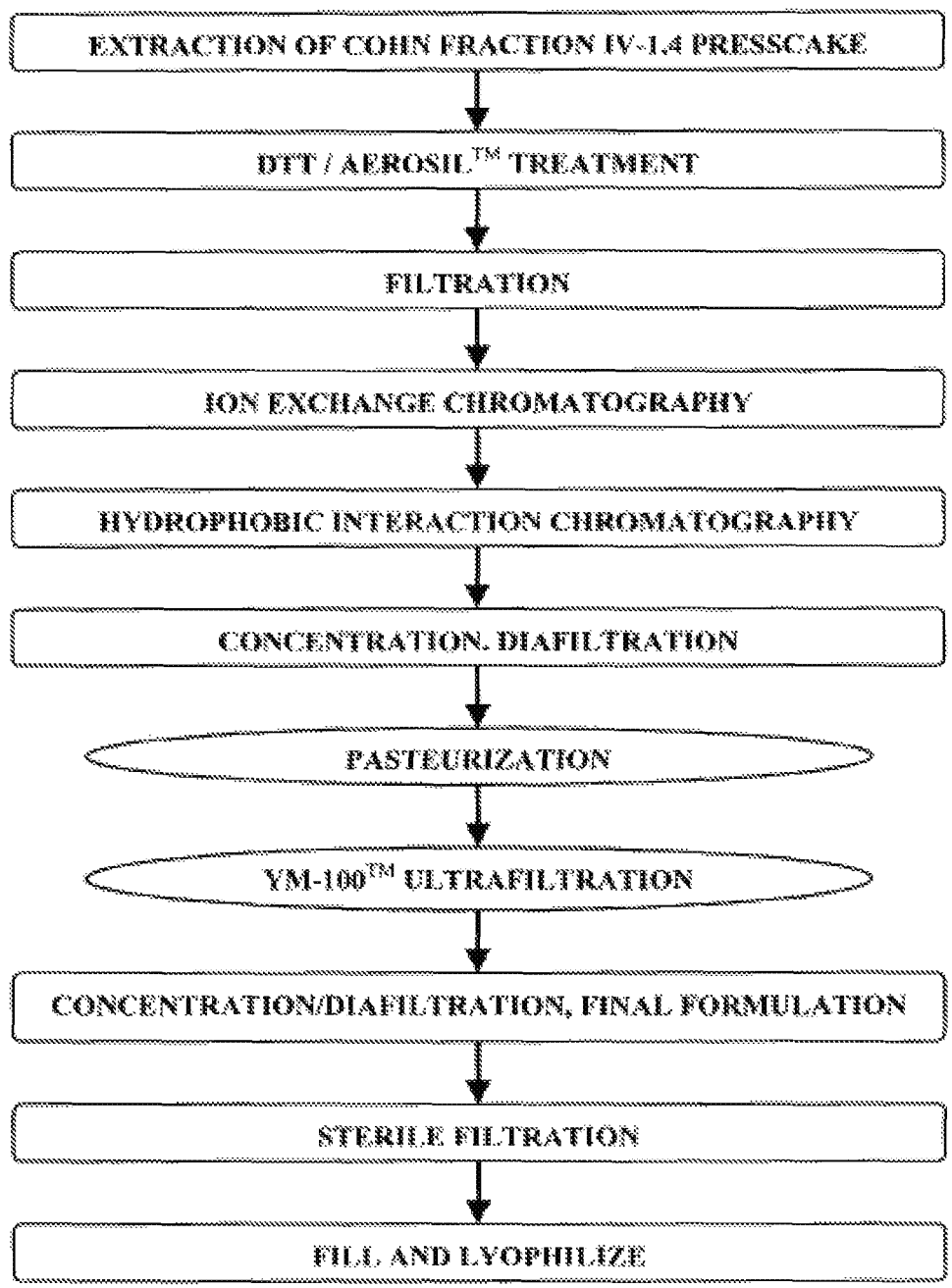
FIG. 1 is a flow chart showing an overall AAT purification process that incorporates the present invention.
Figure 2:
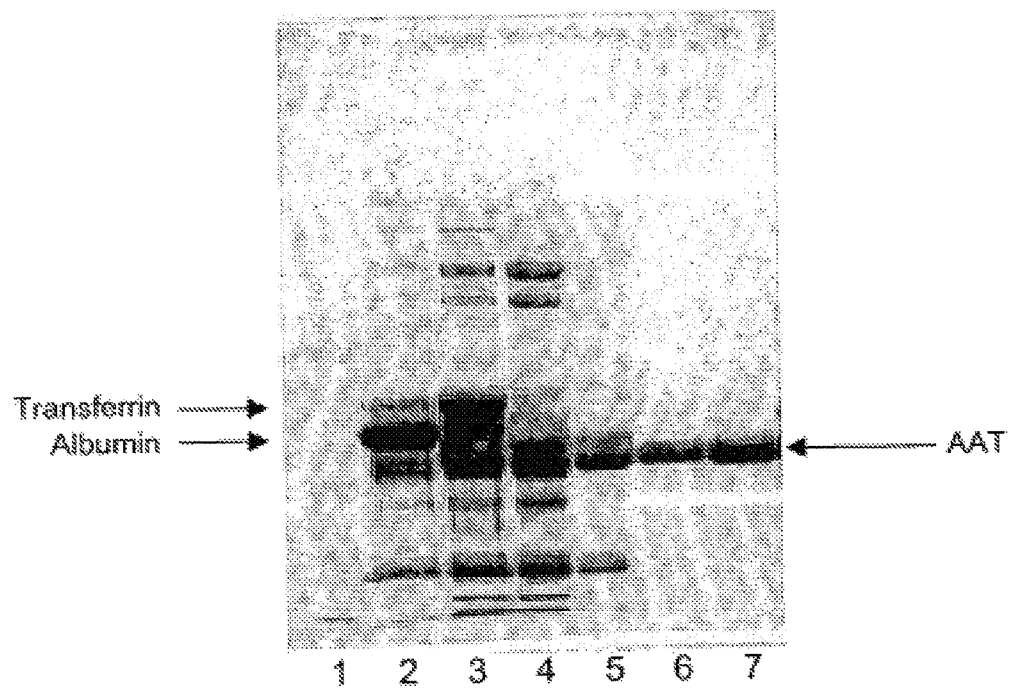
FIG. 2 is an SDS-PAGE gel showing the proteins present in the products produced by the process of the invention at various stages. Lane 1, molecular weight markers; Lane 2, Plasma (Cryo-Poor); Lane 3, Fraction IV$_{1-4}$ Extract; Lane 4, DTT/AEROSIL®-Treated Extract Filtrate; Lane 5, IEC Eluate; Lane 6, HIC Effluent; Lane 7, final container.

The particular embodiment of the invention exemplified below employs a particular Cohn fraction IV paste as a starting material, but the use of similar plasma fractions is contemplated to be within the scope of the present invention. Alternative starting materials include but are not limited to other AAT-containing Cohn fractions (see U.S. Pat. No. 4,697,003), a precipitate from Kistler-Nitschmann supernatants A or A+I (P. Kistler, H. S. Nitschmann, *Vox Sang.*, 7:414-424 (1962)), and ammonium sulfate precipitates from plasma as described by Schultze et al. in U.S. Pat. No.

3,301,842. The use of protein precipitates derived from cultures of AAT-producing recombinant cells or organisms, or precipitates derived from the milk or serum of transgenic mammals, is also contemplated to be within the scope of the present invention.

There are many methods known in the art for selectively precipitating proteins from solution, such as by the addition of salts, alcohols, and polyethylene glycol, often in combination with cooling and various pH adjustments. It is anticipated that the present invention will be applicable to most AAT-containing protein precipitates containing recoverable AAT activity, regardless of how they are initially prepared. The term "crude AAT-containing protein precipitate" is used herein to refer to any AAT-containing protein precipitate prepared by one or more of these known methods, whether from serum, milk, cell culture, or other original source.

In a preferred embodiment, described below, the crude AAT-containing protein precipitate is suspended in a Tris buffer, and treated with dithiothreitol (DTT, a preferred disulfide-reducing agent) and fumed silica (a preferred protein-adsorbing material) in order to remove contaminating proteins and lipids. Where the precipitate is Cohn fraction IV, the two major protein contaminants thus removed are albumin and transferrin. DTT and other dithiols, as well as phosphines, are known in the art to reduce intrachain and inter-chain disulfide bonds. Cleavage of structurally important disulfide bonds causes partial unfolding and destabilization of those contaminating proteins that have disulfide bonds. AAT itself is not destabilized by DTT treatment because it has no intrachain disulfide bonds.

Fumed silica is known to bind preferentially to hydrophobic proteins. It is theorized that in the method of the invention, the destabilized contaminating proteins bind to a protein-adsorbing material such as fumed silica because the partial unfolding caused by disulfide bond cleavage exposes the proteins' inner core of hydrophobic residues. The scope of the invention is not limited, however, to any particular theory of operation.

In a preferred embodiment, described below, the protein-adsorbing material, together with the adsorbed contaminating proteins, lipids, and other insoluble material, is removed from the suspension by filtration so as to obtain a clarified AAT-containing protein solution. Filtration is preferably carried out with the assistance of a filtering aid such as CELITE™ diatomaceous earth, and preferably the suspension is recirculated through the filter until a clarity of <10 nephelometer turbidity units (NTU)/ml is achieved. The filtrate is further processed by chromatographic techniques to afford highly pure and highly active AAT. Other methods of separation known in the art, for example centrifugation, could also be employed in place of filtration. The practitioner will select the method appropriate to the scale of operations and the nature of the protein-adsorbing material.

After removal of insoluble materials, the AAT-containing solution may be further processed by any of the methods known in the art for protein purification, particularly the methods already known to be suitable for purification of AAT. In a preferred embodiment described below, the filtrate is first subjected to ion exchange chromatography ("IEC") with salt gradient elution. The chromatography column contains an anion exchange resin which consists of a porous resin support matrix to which positively charged groups are covalently attached. These positively charged groups reversibly bind anions, including proteins with anionic groups such as AAT.

AAT, and other proteins which have a net negative charge at the pH of the eluting buffer, bind to the IEC column. Contaminating proteins having little or no negative charge pass through the anion exchange resin column without binding and exit with the column effluent. Those contaminating proteins that do bind to the column are then separated from the AAT by gradient elution. The salt concentration is gradually increased as the column is eluted in order to release sequentially the various proteins that are bound to the resin.

In a preferred embodiment, described below, the AAT-containing eluate from the IEC column is subjected to hydrophobic interaction chromatography ("HIC"). This type of chromatography employs a support matrix to which moieties are covalently attached. In an aqueous environment, these hydrophobic moieties bind reversibly to hydrophobic molecules, such as the contaminating proteins remaining in the IEC eluate. AAT is relatively non-hydrophobic, therefore the majority of the AAT flows through the column during the elution of the column with buffer, while the more hydrophobic contaminating proteins remain bound to the column. The column effluent thus contains the purified AAT. In practice, AAT has been found to have a slight affinity for certain HIC column media, and in such cases further elution with several volumes of wash buffer may be desirable in order to recover substantially all of the AAT in the originally-applied sample.

After such additional purification steps as are required to reach the desired level of purity and activity, the AAT solution is then concentrated and sterilized. In a preferred embodiment, described below, the AAT is at a pharmaceutically acceptable level of purity and activity after the hydrophobic interaction chromatography, and no additional steps are necessary. In a preferred embodiment, described below, concentration is accomplished by ultrafiltration followed by dialysis filtration (diafiltration). In these techniques, solvent and dissolved salts and small molecules are passed through a filtering membrane, leaving behind a more concentrated protein solution. Remaining salts and small molecules in the protein solution are then exchanged with a different buffer by continuous addition of several volumes of the new buffer to the product, while maintaining a constant product volume by continuously passing solution through the same membrane.

The AAT is then provided with a pharmaceutically acceptable buffer, and lyophilized by methods known in the art, preferably by methods known to be suitable for preparing AAT therapeutic formulations.

Proteins isolated from mammalian sources may contain pathogenic viral contaminants, and it is desirable to reduce or eliminate such contamination in pharmaceutical compositions. Methods of viral reduction are known to those of skill in the relevant arts. The methods contemplated to be applicable to the present invention include, but are not limited to, pasteurization, irradiation, solvent/detergent treatment, disinfection, filtration, and treatment with supercritical fluids. Solvent/detergent treatment can be carried out, for example, by contacting a protein solution with a polyoxyethylene sorbitan ester and tributyl phosphate (see U.S. Pat. No. 4,820,805; see also WO 95/35306 for application of the method to an AAT composition.) Disinfection of a protein solution can be carried out by exposing the solution to a soluble pathogen inactivating agent, for example as disclosed in U.S. Pat. Nos. 6,106,773, 6,369,048 and 6,436,344, or by contact with an insoluble pathogen inactivating matrix, for example as disclosed in U.S. Pat. No. 6,096,216 and references therein. Filtration may be through 15-70 nm ultrafilters (e.g., VIRA/GARD™ filters, A/G Technology Corp.; PLANOVA™ filters, Asahi Kasei Corp.; VIRESOLVE™ filters, Millipore Corp.; DV and OMEGA™ filters, Pall Corp.). Irradiation may be with ultraviolet or gamma radiation; see for example U.S. Pat. No. 6,187,572 and references therein. Inactivation of viruses by treatment with supercritical fluids is described in U.S. Pat. No. 6,465,168. Pasteurization of a protein solution may be accomplished by heating within the limits dictated by the thermal stability of the protein to be treated. In the case of AAT, pasteurization is usually accomplished by heating to about 60-70° C. In a preferred embodiment, described below, viral reduction of the AAT concentrate is carried out by pasteurization and ultrafiltration. Stabilizing additives may be added to protect the AAT from thermal degradation during the pasteurization step, as disclosed for example in U.S. Pat. No. 4,876,241. Sucrose and potassium acetate are preferably added as stabilizers, and the stabilized AAT solution is then pasteurized at about 60° C. to reduce viral contamination. The amount of sucrose is preferably at least 40%, more preferably at least 50%, and most preferably about 60% by weight. Use of less than 40% sucrose has been found to result in undesirable levels of aggregation of the AAT. The amount of potassium acetate is preferably at least 4%, more preferably at least 5%, and most preferably about 6% by weight.

After viral reduction, the AAT solution may optionally be diluted and ultrafiltered, then re-concentrated and sterilized, e.g. by filtration. The sterilized AAT-containing concentrate may then be lyophilized to form a therapeutic product. A suitable composition for preparing a lyophilized AAT powder is shown in Table 1.

TABLE 1

Composition of AAT solution for lyophilization

| Component | Function | Concentration 1.0 g/vial |
|---|---|---|
| AAT[a] | Active Ingredient | 50 mg/mL[b] |
| Sodium Phosphate[c] | Buffer, Tonicity | 20 mM |
| Sodium Chloride USP | Tonicity | 40 mM |
| Mannitol USP | Stabilizing Agent | 3% |
| Sodium Hydroxide | To adjust pH | as needed |
| Hydrochloric Acid ACS | To adjust pH | as needed |
| Water for Injection USP[d] | Diluent/Vehicle | 20 ml/vial |

[a]The final product is ≥96% AAT as determined by SDS-PAGE and ≥93% monomer by HPLC.
[b]Functional AAT activity per ml.
[c]Added as Monobasic Sodium Phosphate Monohydrate or Dibasic Sodium Phosphate.
[d]Added as Sterile Water for Injection USP.

The final formulation will depend on the viral inactivation step(s) selected and the intended mode of administration. Depending on whether the AAT is to be administered by injection, as an aerosol, or topically, the AAT may be stored as a lyophilized powder, a liquid, or a suspension. The composition shown in Table 1 is suitable for injection, and may be lyophilized and stored in glass vials for later reconstitution with sterile water. The composition of a suitable dry powder formulation for inhalation is shown in Table 2. Such a formulation is suitable for inhalation administration as described in U.S. Pat. No. 5,780,014, either with a metered dose inhaler, or with a pulmonary delivery device such as is disclosed in U.S. Pat. No. 6,138,668.

TABLE 2

Composition of AAT Formulation for Aerosol Administration

| Component | Function | Nominal Content (per unit dose) |
|---|---|---|
| AAT | Active Ingredient | 7.440 mg* |
| Sodium Citrate | Buffer | 0.059 mg |
| Citric Acid | Buffer | 0.001 mg |

*corresponds to 6 mg functional AAT, and a delivered dose of approximately 3.6 mg functional AAT.

Assays for determining the quantity and quality of AAT are known in the art and may be employed for evaluating the efficiency of the method. An example of an immunoassay involving a monoclonal antibody specific for AAT, used for measuring or detecting AAT in biological fluids, is disclosed in U.S. Pat. No. 5,114,863. An example of the use of rate nephelometry is disclosed in L. Gaidulis et al., *Clin. Chem.* 29:1838 (1983). AAT functional activity may be assayed by measuring its elastase inhibitory capacity using a chromogenic substrate for elastase, as described in U.S. Pat. No. 4,697,003. AAT may also be assayed by measuring its trypsin inhibitory capacity in a similar manner. In a preferred embodiment, AAT is assayed by endpoint nephelometry, as described elsewhere in this specification.

The quantity of proteins may be determined by methods known in the art, for example the Bradford assay, or by absorbance at 280 nm using as an extinction coefficient $\Sigma_{1\ cm,\ 280\ nm}^{1\%} = 5.3$ (R. Panned, D. Johnson, and J. Travis, *Biochemistry* 13:5439-5445 (1974)). SDS-PAGE with staining and densitometry may be used to assess purity of the sample and detect the presence of contaminating proteins. A reducing agent such as dithiothreitol is preferably used with SDS-PAGE to cleave any disulfide-linked polymers, thereby facilitating the comparison of total AAT to total non-AAT protein. Size-exclusion HPLC may also be used to assess purity of the sample and detect the presence of both contaminating proteins and aggregate or polymeric forms of AAT. Analysis of four lots prepared by the method of the invention showed AAT protein purity by SDS-PAGE (reduced) of at least 98%, an AAT monomer content of at least 95%, and specific activity averaging 1.06 mg functional AAT/mg protein (Table 3).

TABLE 3

Purity of AAT

| Lot | % AAT Purity by SDS-PAGE (reduced) | % Monomeric AAT by HPLC | Specific Activity (mg functional AAT/mg) |
|---|---|---|---|
| A | 98 | 95 | 1.10 |
| B | 99 | 95 | 1.09 |
| C | 98 | 95 | 1.05 |
| D | 98 | 96 | 1.04 |

Preferred conditions for the methods of the invention are as follows:

1. Preparation of Cohn Fraction IV$_{1-4}$

Human plasma is cooled to −2 to 2° C. and adjusted to a pH of 6.9 to 7.5. Cold ethanol is added to a concentration of 6 to 10%, and the temperature is lowered to −4 to 0° C. The precipitate that forms ("Fraction I") is removed by centrifugation or filtration.

The filtrate or supernatant from the above procedure is adjusted to pH 6.7 to 7.1, and cold ethanol is added to a concentration of 18 to 22%. The temperature is lowered to −7 to −3° C., and the mixture is again subjected to centrifugation or filtration. The precipitate that forms ("Fraction II+III") is set aside for other purposes.

The filtrate or supernatant from the above procedure is adjusted to pH 4.9 to 5.3 and the ethanol concentration is adjusted to 16 to 20%. The temperature is adjusted to −7 to −3° C. After the suspension settles, it is adjusted to pH 5.7 to 6.1 and the ethanol concentration is adjusted to 40 to 44%. The precipitate that forms ("Fraction $IV_1 0.4$") is removed by centrifugation or filtration, and stored until needed in the form of a paste. Fraction $IV_{1-4}$ contains AAT as well as contaminating proteins and lipids.

2. Purification with DTT and Silica

The Fraction $IV_{1-4}$ paste is suspended in a suspension buffer (e.g., 100 mM Tris, 20 mM NaCl, pH between about 7.5 and about 9.5, preferably between about 8 and about 9) and stirred for a minimum of one hour at low temperature. The amount of buffer used ranges from 6 to 10 kg of buffer per kg of the plasma-containing fraction.

The Tris buffer suspension is then treated with dithiothreitol (DTT) and fumed silica. DTT is added to the Tris buffer suspension at a concentration in the range of about 10-50 mM. The solution is stirred for at least 30 minutes, preferably 2-4 hours, at low temperature, and preferably at a pH of about 8-9. Fumed silica is added at a concentration of approximately 100-300 g fumed silica per kg Fraction IV precipitate. The suspension is stirred for at least 30 minutes, preferably 1-4 hours, at low temperature, at a pH of about 8-9. A filter aid such as CELITE™ (diatomaceous earth) is added at the rate of five parts filter aid one part silica, by weight, and the mixture is stirred for approximately 15 minutes. The soluble AAT product is separated from the precipitated fumed silica and contaminating proteins using a filter press, yielding the AAT final filtrate. Preferably, the suspension is recirculated through the filter press until the desired level of clarity is obtained. The AAT final filtrate is then treated further as follows.

3. Ion Exchange Chromatography

The AAT final filtrate is applied directly onto a chromatography column containing an anion exchange resin equilibrated with an IEC equilibration buffer. Contaminants are removed from the column by washing the column with an IEC wash buffer, and AAT is subsequently eluted using an IEC elution buffer.

4. Hydrophobic Interaction Chromatography (HIC)

The eluate from the IEC column is prepared for HIC by adding ammonium sulfate to a final concentration of about 1 M. The solution is then filtered and applied to a hydrophobic interaction chromatography column which is equilibrated in a HIC wash buffer. Initial elution with a wash buffer provides an AAT-containing effluent, and elution with additional wash buffer removes any AAT retained on the column. The combined effluent and washes are concentrated by ultrafiltration, and diafiltered into a phosphate buffer. The final AAT concentration is preferably no greater than 7% protein.

5. Pasteurization

The AAT concentrate is stabilized for pasteurization by the addition of sucrose and potassium acetate, and pasteurized at about 60° C. for 10-11 hours. The pasteurized solution is held at 2-8° C. pending further processing.

6. Nanofiltration

The pasteurized AAT solution is diluted with a final formulation buffer. The diluted, pasteurized AAT solution is then filtered through two new YM-100 (Amicon) spiral-wound ultrafiltration cartridges. This nanofiltration step serves as a second primary viral reduction step. Viruses are retained by the membrane, which has a nominal 100,000 Dalton molecular weight cut-off, while AAT, which has an approximate molecular weight of 50 kD, passes through. The AAT is collected in the permeate of the second filter and in filter post-washes. The final filtrate is collected in a bulk receiver and held at 2-8° C.

7. Sterile Filtration and Lyophilization

The AAT-containing final filtrate is concentrated and diafiltered into final formulation buffer at a temperature of no more than 15° C. to form a final bulk solution. This solution is clarified and sterilized by passage through a series of sterile, bacterial-retentive filters. The sterile bulk solution is filled into sterilized glass final containers. The filled containers are freeze-dried and then sealed under vacuum.

The product is ≥96% pure AAT as determined by both SDS-PAGE and immunological assays such as ELISA or nephelometry, and is ≥93% monomer by size exclusion HPLC. The recovery based on the functionally active AAT content of the Cohn fraction IV paste is 70%.

EXAMPLES

Fraction $IV_{1-4}$ Precipitate (667 kg) was isolated via the Cohn plasma fractionation process from 9026 liters of human plasma. The material was divided into nine batches of approximately 75 kg each. Each batch was suspended in Tris Buffer, using 6 to 10 parts buffer (w/w) relative to the presscake. The suspensions were stirred for at least 15 minutes, the temperature was adjusted to 2°-8° C., and the pH of each suspension was adjusted to 8.80-8.95 with 1 $\underline{N}$ sodium hydroxide or 1 $\underline{N}$ hydrochloric acid as necessary. The suspensions were stirred for 15 to 105 minutes (average 45 min), and monitored for protein (Bradford assay) and potency. Specific activity of each batch ranged from 0.027 to 0.045, and averaged 0.037 mg functional AAT per mg protein. Approximately 12% of the total protein was albumin, and approximately 22% was transferrin.

Dithiothreitol (DTT) was added to a final concentration of 0.01 to 0.05 M DTT (average 0.03 $\underline{M}$) based upon the amount of Tris Buffer in each batch. After a pre-mix period of at least 15 minutes, the temperature was adjusted to 2°-8° C. and the pH re-adjusted to 8.80-8.95, and the solutions were stirred for 2 to 8 hours (average 3 hours). If necessary, the pH was again adjusted to 8.80-8.95.

AEROSIL® 380 (fumed silica, Degussa AG, Frankfurt-Main) was added at the rate of 13.4 to 18.6 g per liter plasma input (average 16.7 g). The suspensions were stirred for 1 to 4 hours (average 1 hour) at 2-8° C.

CELITE™ 545 was added to each suspension at the rate of 5 parts CELITE™ to 1 part AEROSIL®, and the suspensions were stirred at 2-8° C. Each suspension was then recirculated through a plate and frame filter press, holding 25×25 inch CUNO™ A2605—10CP filter pads (cellulose pads with inorganic filter aids; nominal cutoff 1 micron). When the turbidity was ≤10 NTU by nephelometry (minimum of 15 min.), recirculation was discontinued and the filtrate was collected. The filter press was post-washed with TRIS extraction buffer at 2-8° C. The postwashes were combined with the initial filtrate solutions, and total protein in solution was determined by the Bradford protein assay. The filtrates were held at 2-8° C. for no longer than 19 hours. Based on AAT activity, the filtrates contained a total of 1557 g of ATT, corresponding to a 59% yield of the activity present in the original suspension of Fraction IV paste, and a purification factor of 1.5. (In view of the activity present after subsequent processing, these values appear to be low, possibly due to the presence of unidentified factors interfering with the AAT assay.) Specific activity for each of the nine batches ranged from 0.042 to 0.064, and averaged 0.056 mg functional AAT per mg protein. Albumin and transferrin were below detection limits (total protein contained less than 0.5% albumin and less than 2.5% transferrin.)

A 92-liter, 30 cm high ion exchange chromatography (IEC) column loaded with TMAE FRACTOGEL™ (synthetic polymeric resin media, EM Industries, Hawthorne, N.Y.) was equilibrated with IEC equilibration buffer (50 mM Tris, pH 8.3-9.3, 20-25° C.). Following equilibration, conductivity of the effluent was verified to be ≤1.25 mS/cm. Each filtrate from the previous step was warmed to 20-25° C. and filtered through a CUNO ZETA PLUS™ 90SP cartridge (45115-12-90SP, depth filter cartridge, nominal MW cutoff of 0.1 micron) before loading onto the column with control of flow rate (≤3.0 cm/minute) and column pressure ≤20 psi). Total protein loaded onto the IEC column was limited to no more than 70% of the resin capacity. The column was then washed with five column volumes of IEC wash buffer (50 mM Tris, 25-70 mM NaCl gradient, pH 7.1-7.7) at 20-25° C., with control of flow rate (≤3.0 cm/minute) and column pressure (≤20 psi). The effluent was monitored by Bradford protein determination, assay of AAT activity, and UV absorbance at 280 nm.

AAT was eluted with approximately three column volumes of IEC elution buffer (50 mM Tris, 75-120 mM NaCl gradient, pH 7.1-7.7) at 20-25° C., with control of flow rate (≤3.0 cm/minute) and column pressure (≤20 psi). The effluent was monitored by Bradford protein determination, assay of AAT activity, and UV absorbance at 280 nm. The entire peak that eluted after application of the elution buffer was collected for further processing.

The above procedure was repeated nine times in order to process all nine batches of filtrate. Ammonium sulfate was added to the IEC eluates to a final concentration of 0.9 to 1.1 M. The resulting solutions were either used immediately, or stored at 15-25° C. for no more than seven days. Based on AAT activity, the IEC eluates contained a total of 2241 g of ATT, corresponding to an 84% yield of the activity present in the original suspension of Fraction IV paste, and a purification factor of 16.2. Specific activity for each of the nine batches ranged from 0.416 to 0.975, and averaged 0.592 mg functional AAT per mg protein.

A CUNO™ filter (ZETA PLUS™ 90SP cartridge 45115-12-90SP, nominal MW cutoff of 0.1 micron) was prepared with a hot WFI flush followed by a cold WFI rinse (WFI=Water for Injection). Water was gently blown out of the filter with compressed air. Three IEC eluates, containing ammonium sulfate, were pooled and filtered through the prepared CUNO™ filter and subsequently combined to provide the "filtered IEC solution". The filter was postwashed with approximately 20 liters HIC wash buffer (50 mM Tris, 1 M ammonium sulfate, pH 7.7). The post-wash and the filtrate were combined and weighed. The process was repeated three times to process the nine batches of IEC eluate.

A hydrophobic interaction column (HIC) was packed with PHENYL SEPHAROSE™ Fast Flow HS resin (Pharmacia, Piscataway, N.J.) to a volume of 49 liters (32 cm bed height), and equilibrated with HIC wash buffer (50 mM Tris, 1 M ammonium sulfate, pH 7.1-7.7). This and all column loading and subsequent elutions were carried out with control of flow rate ≤4 cm/minute, column pressure ≤20 psi), and solution temperatures (20-25° C.).

Each of the three batches of filtered IEC solution was loaded onto an HIC column. Total protein load onto the column was limited to ≤39 g protein per liter of resin. Optical density ($OD_{280}$) of the effluent was monitored, and collection was initiated when the $OD_{280}$ rose 0.04 units higher than the baseline value. The column was washed with HIC wash buffer to elute additional AAT from the column, while non-AAT contaminants remained bound to the column. Approximately ten column volumes of HIC wash buffer was applied to the column, and effluent was collected until the $A_{280}$ dropped to <0.05 units above baseline. The AAT effluent and column wash were combined and weighed. Samples were taken for Bradford protein determination, OD Protein determination, potency, and LAL (Limulus amebocyte lysate) testing. The HIC effluents were held at 15-25° C. for no more than 72 hours. Based on AAT activity, the three batches of HIC effluent contained a total of 2090 g of ATT, corresponding to a 79% yield of the activity present in the original suspension of Fraction IV paste, and a purification factor of 25.6. Specific activity for each of the three batches ranged from 0.908 to 0.986, and averaged 0.937 mg functional AAT per mg protein.

A tangential flow ultrafiltration (UF) unit containing a polyether sulfone membrane (surface area: 50 ft$^2$) with a molecular weight cut off range of 5,000-30,000 was integrity tested to ensure a bubble point of less than 1250 ml/minute. Diafiltration buffer (40 mM sodium phosphate, pH 7.2-7.6; 10 kg minimum) was recirculated through the unit for a minimum of five minutes. The recirculated buffer solution was sampled to verify proper pH (7.2-7.6) and LAL (<0.25 EU/ml). A repeat of the prewash steps was performed if pH and LAL requirements were not met. The UF unit was held for no more than 12 hours at 2-8° C. prior to HIC Effluent application.

The HIC effluent from the previous process step was mixed, and the temperature was adjusted to 15-25° C., prior to application to the ultrafiltration unit. Inlet pressure was maintained at ≤40 psi, and outlet pressure and sample weight were monitored during the concentration process. Concentration was performed until the weight of the concentrate was approximately 10 kg.

Following concentration, the HIC effluent concentrate was diafiltered, exchanging the Tris-buffered ammonium sulfate solution with a sodium phosphate buffer. Diafiltration buffer (40 mM sodium phosphate, pH 7.2-7.6) was applied at a volume ten times the weight of the HIC effluent concentrate. Inlet pressure was maintained at <40 psi, and outlet pressure was monitored. After all of the diafiltration buffer had been added, the sodium concentration of the permeate was determined. Diafiltration was considered complete if the sodium concentration of the permeate was within 10% of that of the diafiltration buffer. Additional diafiltration buffer (5× the weight of the concentrate) was added, and diafiltration extended, if necessary, until the sodium concentration of the permeate was within 10% of that of the diafiltration buffer.

Following diafiltration, the ultrafiltration was continued until the concentrate had a mass of approximately 6 kg. Product was then gently blown out of the UF system (≤25 psi). The ultrafiltration unit was postwashed twice with 1.5 kg diafiltration buffer. The UF postwashes were added to the diafiltered concentrate. The total weight of concentrate was determined and the protein concentration determined (OD at 280 nm).

Based on the OD protein observed, the AAT protein concentration was determined, and adjusted if necessary to the range 2.9-6.8%. Analysis for LAL, SDS-PAGE, Bradford protein, potency, and bioburden were performed. SDS-PAGE showed ≥98% AAT. Based on AAT activity, the concentrates contained a total of 2096 g of AAT, a 79% yield of the activity present in the Cohn paste suspension, and a purification factor of 26.6. Specific activity for each of the three batches ranged from 0.886 to 1.04, and averaged 0.974 mg functional AAT per mg protein.

The AAT concentrate (2.9-6.8% protein) was adjusted to 20-25° C., and sucrose (1.75 kg per kg AAT concentrate) and potassium acetate (0.175 kg per kg AAT concentrate) were added. The final concentration of sucrose was 59.8%±6% (w/w), and the final concentration of potassium acetate was 5.98%±0.6% (w/w). After mixing, the stabilized concentrate was transferred into one-liter sealed serum bottles. The bottles were stored at 2-8° C. for no more than 10 weeks (and at 15-25° C. for no more than 48 hours) before being heat-treated (pasteurized). Pasteurization at 60±1° C. was performed for 10-11 hours. The pasteurized AAT solution was held at 2-8° C. for no more than 10 weeks, and at 15-25° C. for no more than 72 hours, prior to further processing.

Pasteurized AAT solution was pooled under HEPA-filtered air into two batches, and diluted with diafiltration buffer (20 mM sodium phosphate, 45 mM NaCl, 3% mannitol, pH 6.6-7.4) at a ratio of 5:1 buffer:AAT solution (w/w). The diluted solutions were sampled for LAL, protein, and potency. Based on AAT activity, the pasteurized and diluted solutions contained a total of 1941 g of AAT, a 73% yield of the activity present in the Cohn paste suspension, and a purification factor of 26.6. Specific activities for the two pasteurized batches were 0.954 and 0.993, an average of 0.973 mg functional AAT per mg protein. The percent monomer of the AAT solutions was measured by size-exclusion HPLC before and after pasteurization. The monomer fractions of the AAT concentrates (pre-pasteurization) were 97.1% to 98.5%, averaging 97.7%. The monomer fractions of the two pasteurized and diluted solutions were 95.9% and 97.5%, an average of 96.7%. Only 1.0% of the monomeric form of AAT was polymerized or aggregated during the pasteurization step.

Two YM100 filter cartridges (Millipore, Bedford, Mass.) were installed in series into a YM100 UF system, with the first cartridge operated in a tangential flow mode and the second cartridge dead-ended. The UF system was recirculated with a minimum of 5 kg diafiltration buffer. Following recirculation, the diafiltration buffer was tested to verify pH (6.8-7.2) and LAL (<0.25 EU/ml). The diafiltration buffer, and all subsequent processing until lyophilization, was at 2-8° C.

Each of the pooled AAT solutions was passed through the YM100 cartridges at 2-8° C. at an inlet pressure of ≤45 psi. The load did not exceed 1339 grams protein, and the weight of the YM100 filtrate plus postwashes did not exceed 337 kg. The YM100 filtrates were then ultrafiltered and diafiltered, at an inlet pressure of ≤50 psi, against diafiltration buffer (1.60-1.90 mg/ml sodium, 10 times the YM100 concentrate weight), using an ultrafilter containing a 10,000 M.W. membrane (≥25 ft² surface area) that was dedicated to the post-pasteurization process.

The diafiltered solutions were sampled inline and tested for sodium. If the sodium level of the permeate was within ±10% of the diafiltration buffer sodium concentration, diafiltration was considered complete. If the sodium level was not within ±10% of the diafiltration buffer sodium concentration, diafiltration was repeated with additional diafiltration buffer (5 times the YM100 filtrate weight).

A final concentration was performed until approximately 6 kg of solution was obtained. Two postwashes were performed using 1.5 kg diafiltration buffer each time. Postwashes were combined with the concentrate for determination of total volume of diafiltered YM100 filtrate. Diafiltered YM100 filtrates were held for no more than 12 days at 2-8° C. before further processing. Based on AAT activity, the diafiltrate contained a total of 1960 g of AAT, a 74% yield of the activity present in the Cohn paste suspension, with a purification factor of 27.5. Specific activities for the two batches were 0.984 and 1.03, an average of 1.01 mg functional AAT per mg protein.

After addition of diafiltration buffer to obtain a final formulation target of 50 mg functional AAT/ml, the YM100 filtrate solution pH was adjusted as necessary to pH 6.8-7.2. Clarification was carried out with a 0.2 micron Pall SLK-7002-NRP Filter (Pall Corp., East Hills, N.Y.). Once clarified, the non-sterile bulk AAT solutions were combined, weighed and sampled for LAL, protein, potency, and bioburden (≤100 CFU/ml). The non-sterile bulk AAT was held for no longer than 73.5 hours at 2-8° C. pending sterile filtration. Based on AAT activity, the non-sterile bulk AAT solution contained a total of 1822 g of AAT, a 69% yield of the activity present in the Cohn paste suspension, with a purification factor of 26.8. The specific activity was 0.981 mg functional AAT per mg protein.

In preparation for sterile filtration, a sterile bulk assembly consisting of a 60 L bulk receiver, a Pall 0.2 micron KA1NFP2 sterilizing filter and two (2) Millipore 0.2 Micron AERVENT™ 50 vent filters (hydrophobic polytetrafluoroethylene filters) was prepared. The assembly was autoclaved and used within 7 days of autoclaving. The non-sterile bulk solution was sterile-filtered with control of temperature (2-8° C.), pressure (≤20 psi), filtration time (≤120 minutes), and load including postwash (≤0.26 kg non-sterile bulk per cm² filter area). The sterile filtrate ultimately obtained from 667 kg of Cohn fraction IV paste contained 1.78 kg of functional AAT, corresponding to an overall yield of 67% based on the activity of the initial Cohn fraction $IV_{1-4}$ suspension, and a purification factor of 29.8. The specific activity was 1.09 mg functional AAT per mg protein. The product was >99% AAT by SDS-PAGE, and >95% monomer by size-exclusion HPLC.

AAT sterile bulk was aseptically filled into 50 ml Type I glass vials using a fill volume targeted to achieve approximately 1000 mg functional AAT activity per vial (i.e. 20.8 g±0.2 g solution per vial), and the vial contents were frozen and lyophilized.

TABLE 4

| | Fr. $IV_{1,4}$ | Post-Aerosil | Filtrate | IEC Eluate | HIC Effluent | DF HIC Conc. | Diluted, Pasteur. | YM100 | Non-Sterile | Final Container |
|---|---|---|---|---|---|---|---|---|---|---|
| No. of Batches | 9 | 9 | 9 | 9 | 3 | 3 | 2 | 2 | 1 | 1 |
| Yield (g AAT; total for all batches) | 2658 | 1833* | 1557* | 2241 | 2090 | 2096 | 1941 | 1960 | 1822 | 1780 |

TABLE 4-continued

|  | Fr. IV$_{1,4}$ | Post-Aerosil | Filtrate | IEC Eluate | HIC Effluent | DF HIC Conc. | Diluted, Pasteur. | YM100 | Non-Sterile | Final Container |
|---|---|---|---|---|---|---|---|---|---|---|
| Overall Yield from Extract | 100% | 69% | 59% | 84% | 79% | 79% | 73% | 74% | 69% | 67% |
| Purification Factor | 1.0 | 1.4 | 1.5 | 16.2 | 25.6 | 26.6 | 26.6 | 27.5 | 26.8 | 29.8 |
| Specific Activity** (mg/mg) | 0.037† | 0.053† | 0.056† | 0.592† | 0.937‡ | 0.974‡ | 0.973‡ | 1.01‡ | 0.981‡ | 1.09‡ |

*The AAT assay for these fractions is believed to be low, due to unidentified interfering factors.
**Specific activities are averages over the number of batches shown.
†The Bradford Protein assay was used for these fractions because they are too impure to determine protein concentration by OD$_{280}$. The protein standard used in the Bradford assay was purified AAT, calibrated using an extinction coefficient for AAT of 5.3, see R. Pannell, D. Johnson, and J. Travis, *Biochemistry* 13: 5439-5445 (1974).
‡Protein concentration by OD$_{280}$ using an extinction coefficient for AAT of 5.3.

Functional AAT yields, and characteristics of the AAT fractions obtained, at each of the above steps are set out in Table 4.

Modifications of the above-described modes for carrying out the invention will be obvious to those of skill in the fields of protein purification, analytical chemistry, medicine, and related fields, and such substitutions and modifications are contemplated to be within the scope of the invention. The detailed embodiments described above are provided by way of example only, and are not intended to limit the scope of the following claims.

We claim:

1. A method of treating alpha-1-antitrypsin (AAT) deficiency in a subject in need thereof, comprising administering to the subject a pharmaceutically effective amount of a pharmaceutical composition comprising plasma-derived alpha-1-antitrypsin (AAT), wherein said composition further comprises:
   (a) less than 0.1% albumin based on total protein weight;
   (b) less than 0.8% α$_1$-acid glycoprotein based on total protein weight;
   (c) less than 0.1% α$_2$-macroglobulin based on total protein weight;
   (d) less than 0.1% apolipoprotein A1 based on total protein weight;
   (e) less than 0.5% antithrombin III based on total protein weight; and
   (f) less than 0.1% ceruloplasmin based on total protein weight,
   wherein total protein weight is measured using a Bradford assay or by absorbance at 280 nm using as an extension coefficient $E_{1\ cm,\ 280\ nm}^{1\%}=5.3$.

2. The method of claim 1, wherein the apparent ratio of active to antigenic AAT is greater than 1.08 when measured by endpoint nephelometry.

3. The method of claim 1, wherein the specific activity of the AAT is at least 0.99 mg functional AAT per milligram of protein, when using as an extinction coefficient $E_{1\ cm,\ 280\ nm}^{1\%}=5.3$.

4. The method of claim 1, wherein the specific activity of the AAT is less than or equal to 1.12 mg functional alpha-1-antitrypsin per milligram of protein.

5. The method of claim 1, wherein prior to administering the composition to the subject, the composition is subjected to a viral reduction procedure capable of reducing the number of enveloped viruses by at least 11 log$_{10}$ units and capable of reducing the number of non-enveloped viruses by at least 6 log$_{10}$ units, wherein the reduction in the number of viruses is relative to the amount of virus prior to the reduction procedure.

6. The method of claim 1, wherein the composition is stable for at least 2 years when stored lyophilized at ≤25° C.

7. The method of claim 1, wherein the composition is stable for at least 2 years when stored lyophilized at 25° C.

8. The method of claim 1, wherein the composition comprises 6% or less contaminating proteins based on total protein weight and as determined by SDS-PAGE.

9. The method of claim 8, wherein the specific activity of the AAT is at least 0.99 mg functional AAT per milligram of protein, when using as an extinction coefficient $E_{1\ cm,\ 280\ nm}^{1\%}=5.3$.

10. The method of claim 8, wherein the specific activity of the AAT is less than or equal to 1.12 mg functional alpha-1-antitrypsin per milligram of protein.

11. The method of claim 8, wherein prior to administering the composition to the subject, the composition is subjected to a viral reduction procedure capable of reducing the number of enveloped viruses by at least 11 log$_{10}$ units and capable of reducing the number of non-enveloped viruses are reduced by at least 6 log$_{10}$ units, wherein the reduction in the number of viruses is relative to the amount of virus prior to the reduction procedure.

12. The method of claim 8, wherein the composition is stable for at least 2 years when stored lyophilized at ≤25° C.

13. The method of claim 8, wherein the composition is stable for at least 2 years when stored lyophilized at 25° C.

14. The method of claim 8, wherein the composition comprises 2% or less contaminating proteins based on total protein weight and as determined by SDS-PAGE.

* * * * *